(12) United States Patent
Dixon et al.

(10) Patent No.: US 6,482,003 B2
(45) Date of Patent: *Nov. 19, 2002

(54) INDIVIDUAL DOSE DENTAL ADHESIVE DELIVERY SYSTEM AND METHOD

(75) Inventors: Daniel R. Dixon, Villa Park, CA (US); Craig A. Andreiko, Alta Loma, CA (US)

(73) Assignee: Ormco Corporation, Orange, CA (US)

( * ) Notice: Subject to any disclaimer, the term of this patent is extended or adjusted under 35 U.S.C. 154(b) by 46 days.

This patent is subject to a terminal disclaimer.

(21) Appl. No.: 09/825,149

(22) Filed: Apr. 3, 2001

(65) Prior Publication Data

US 2001/0055741 A1 Dec. 27, 2001

Related U.S. Application Data

(63) Continuation-in-part of application No. 09/377,721, filed on Aug. 19, 1999, now Pat. No. 6,213,767.

(51) Int. Cl.[7] .................................................. A61C 3/00
(52) U.S. Cl. ............................ 433/9; 206/309; 401/129
(58) Field of Search .............................. 433/4, 8, 9, 77; 206/572, 368, 369; 601/1; 401/129

(56) References Cited

U.S. PATENT DOCUMENTS

| | | | |
|---|---|---|---|
| 4,952,204 A | | 8/1990 | Korteweg |
| 5,350,059 A | | 9/1994 | Chester et al. |
| 5,354,199 A | | 10/1994 | Jacobs et al. |
| 5,636,736 A | | 6/1997 | Jacobs et al. |
| 5,660,273 A | | 8/1997 | Dicko, Jr. |
| 5,692,896 A | * | 12/1997 | Pospisil et al. ................ 433/8 |
| 5,756,174 A | | 5/1998 | Tuneberg |
| 5,759,028 A | | 6/1998 | Bozman |

* cited by examiner

*Primary Examiner*—Todd E. Manahan
(74) *Attorney, Agent, or Firm*—Wood, Herron & Evans, L.L.P.

(57) ABSTRACT

Individual doses of dental adhesive are dispensed onto a flat conformable card and enclosed under a cover sealed to the card. The cover is peeled off at chairside and individual doses of the adhesive are picked up by a wiping action of a dental tool or of an object to be bonded, such as, for example, by wiping action of an orthodontic bracket base over the adhesive bearing surface of the card. The card deforms to conform to the curvature of the edge of the appliance or object to cleanly transfer all of the adhesive of a dose from the card to the appliance base.

16 Claims, 12 Drawing Sheets

US 6,482,003 B2

1

INDIVIDUAL DOSE DENTAL ADHESIVE DELIVERY SYSTEM AND METHOD

This is a Continuation-in-Part of commonly assigned and copending U.S. patent application Ser. No. 09/377,721, filed Aug. 19, 1999, U.S. Pat. No. 6,213,767, hereby expressly incorporated by reference herein.

FIELD OF THE INVENTION

This invention relates to the delivery of dental adhesives and particularly to the delivery of dental adhesives in small or single dose quantities. The invention is more particularly applicable to the delivery of dental adhesives for the bonding of orthodontic appliances to teeth.

BACKGROUND OF THE INVENTION

Providing dental adhesives to dental practitioners in a form that they can be efficiently used and so that excess quantities are not exposed or wasted has been the subject of a number of efforts. Single dose delivery systems have been developed in which a dental adhesive or composite of a quantity that is no greater than that needed for a single application or as a single dose include, for example, the delivery system described in U.S. Pat. No. 5,860,806, hereby expressly incorporated herein by reference.

With the development of orthodontic brackets such as those described, for example in U.S. Pat. No. 4,068,379, the orthodontic brackets with bases for adhesive bonding to teeth have replaced tooth encircling bands as the primary appliances for connecting orthodontic archwires to teeth. With banded appliances, archwire supports mounted on bands encircle the teeth to hold the archwire supports in place on the teeth. Brackets, on the other hand, rely solely on an adhesive bond between the base or pad of the bracket and the surface of the crown of the tooth. Adequate bond strength between the teeth and the bracket bases has traditionally required the dentist or an assistant to dispense adhesive onto the bracket at chairside, using single or multiple part dental adhesives specifically developed for securing orthodontic appliances to teeth. Popular single part adhesives are cured by ultraviolet light, while multiple part adhesives cure chemically, following the mixing of the adhesive immediately preceding use. Multiple part or chemical cure adhesives are often capable of producing bonds that are stronger than with the light cured adhesives.

The application of adhesives to brackets at chairside is a time consuming activity for a dental or orthodontic practitioner. In preparing adhesive at chairside, the quantity of adhesive dispensed must be carefully controlled by the orthodontist or other office personnel. Cleanup is required, which must be done by the doctor, whose time is expensive. The handling of brackets during the application of adhesive can result in misorientation of the appliances or a mixup of appliances, which are usually each designed to fit a specific tooth.

One attempt to minimize the chairside handling of adhesives in the application of orthodontic appliances to teeth has been the introduction of orthodontic brackets with light cured adhesive pre-applied to the bracket bases. While these brackets with pre-applied adhesive are attractive to orthodontists for their promise of convenience and ease of installation on the teeth of the patient, such brackets have been associated with an increased failure rate of the bond between the bracket bases and the teeth.

One cause of failures of the bonds between the bracket and a tooth is due to the use of an adhesive beyond its actual

2 shelf life. The shelf life of adhesive that has been pre-applied to brackets is optimistically claimed to be twenty-four months. In practice, environmental factors, such as heat, humidity, etc., during transit and storage of the brackets having the pre-applied adhesives, shorten the shelf life of the adhesive. Furthermore, orthodontic brackets with adhesives pre-applied seldom reach the offices of orthodontists immediately following manufacture, so that some portion of the shelf life of the adhesive is already spent by the time the brackets are received into inventory by the orthodontist. In addition, careful records and careful inventory control by the doctor is required to insure that all adhesively pre-coated brackets are used in a first-in first-out (FIFO) basis and before the adhesive becomes too old.

Orthodontic brackets are often stocked by orthodontists in sufficient quantities so that the doctor has available appliances of various types and sizes to use on any common occasion in the treatment of patients. Maintaining appliance inventories necessarily requires that certain appliances will be in inventory longer than others. Ordinarily, orthodontic brackets are made of metal or other materials that have shelf lives that exceed the technological lives of the appliance, that is, the appliance can usually be stored until it is used or becomes obsolete, which can be many years from the stocking of the appliance by the doctor. Orthodontic brackets have a cost of several dollars each to the doctor, for example, four U.S. dollars per bracket at the time of this patent application. The cost of the adhesive used to secure orthodontic brackets to teeth is substantially less than the cost of an ordinary bracket. A single dose of adhesive, that is, the amount of adhesive necessary to secure a single orthodontic bracket to a tooth, varies from a few cents when supplied separately to about a 75 cent/bracket price premium charged by an adhesively pre-coated bracket manufacturer. As a result, the pre-application by a bracket manufacturer of a few cents worth of adhesive to the base of a bracket has the undesirable effect of limiting the shelf life of a relatively expensive orthodontic appliance.

There are additional disadvantages to the adhesively pre-coated orthodontic appliances currently available to orthodontists. The packaging of such appliances, for example, is quite expensive to produce and is bulky. One hundred cases, for example, might occupy several cubic feet of space in a dentist's office, which is equal, for example, to that occupied by a small appliance or piece of furniture. Individual brackets having pre-applied adhesive are packaged in sealed packages which must be individually opened at chairside. Appliance delivery systems cannot readily accommodate these brackets or bracket packages, and separate systems for dispensing adhesive primer must be used. Only one part, light curable adhesives, can be pre-applied to brackets. Use of multiple part adhesives, which can be up to thirty percent stronger, is not practical for use on pre-coated brackets. Furthermore, when the amount of pre-applied adhesive appears to be incorrect in a particular situation, there is no easy way for the orthodontic practitioner to adjust the quantity of adhesive in the dentist's office.

Accordingly, there is a great need on the part of orthodontic practitioners for a system for easily and conveniently applying orthodontic appliances to teeth with adhesive that does not have all of the disadvantages of the pre-adhesively coated orthodontic brackets of the prior art.

SUMMARY OF THE INVENTION

A primary objective of the present invention is to provide a dental practitioner a convenient supply of dental adhesive that can be used with a maximum reliability and efficiency and minimum amount of waste and mess. A particular objective of the invention is to provide such a supply of adhesive to an orthodontic practitioner for use in bonding orthodontic brackets to teeth.

A further objective of the present invention is to provide an orthodontic practitioner the advantages that adhesively pre-coated brackets have over the chairside application of adhesive from bulk sources to orthodontic appliances and overcoming the disadvantages of the adhesively pre-coated brackets of the prior art.

According to principles of the present invention, single doses of dental adhesive are provided on substrates and enclosed over an area of the card with a removable cover. The doses of adhesive are provided by dispensing one or more metered amounts of adhesive, preferably in the form of a high viscosity liquid or a paste, onto an area of the substrate, preferably in the form of a disposable card, over which a protective cover is secured. The cover keeps the adhesive out of contact with objects during shipping and handling, and sufficiently prevents exposure of the adhesive to chemicals or light or whatever other medium would tend to set or cure the adhesive so as to preserve the normal expected shelf life of the adhesive.

In the preferred embodiments of the invention, individual appliance doses of orthodontic adhesive are provided to an orthodontist separate from the orthodontic appliances that the adhesive is designed to bond to teeth. Individual doses of such orthodontic adhesive are provided in a form for direct transfer to the bases of orthodontic appliances at chairside. Further, individual adhesive doses are packaged for easy use, and are presented in combination with, or in an arrangement by which they can be easily associated with, specific orthodontic appliances for each of the teeth of a patient.

In accordance with certain principles of the present invention, there is provided an adhesive delivery system and method in which a substrate is provided having a deformable, compliant or conformable surface that allows an edge of a rigid object to be swiped over the surface and cleanly remove from the surface a single dose of adhesive that has been deposited thereon. On such surface, one or more single dose amounts of adhesive, such as orthodontic or other dental adhesive, are supported on separate transfer areas from which they can be effectively transferred to a rigid object such as a tool, a restoration, or the base of an orthodontic appliance, by contact of the object with the substrate, preferably by such swiping motion of the object along the substrate to efficiently scrape the measured dose of adhesive from the substrate surface onto the object. The substrate is preferably provided with a resilient core and a surface that is relatively low friction, non-stick, non-absorbent, vapor-proof and flexible.

At least one, and preferably one for each appliance of an appliance set or other object, single-dose quantity of adhesive is pre-dispensed onto the substrate surface. The preferred adhesive is a non-volatile liquid or paste dental adhesive. Each dose is pre-dispensed onto an adhesive transfer area on the adhesive supporting surface of the substrate. The adhesive is contained in a cavity over the substrate by a vapor-proof cover that is sealed to the substrate surface so as to form a raised enclosure covering the adhesive transfer area or areas of the adhesive supporting surface. Preferably, a plurality of separate cavities is formed between the cover and the substrate surface, one for each of the adhesive transfer areas and each containing one single dose amount of the adhesive. However, the cover may be configured so that a set or sub-set of doses is sealed in a cavity or volume. Preferably, the cover is configured so as to remain out-of-contact with the adhesive on the adhesive transfer areas of the substrate surface. The cover may be configured to open the cavities and expose the doses individually or to expose several or all of a set of doses simultaneously.

In accordance with certain preferred embodiments of the invention, orthodontic appliance holders are provided, one for each adhesive transfer area, and each holder is configured to hold an orthodontic appliance in a ready position relative to a dose of adhesive for easy pickup by an orthodontist. One holder is preferably provided for the support of each appliance needed to treat a particular patient at a particular sitting. In certain embodiments of the invention, an orthodontic appliance is also provided, and preferably a set of appliances is provided, with each appliance associated with each adhesive transfer area that contains a single appliance dose of adhesive, providing the orthodontist with a complete orthodontic appliance system of the components needed to treat a case. All of the doses may be provided of the same adhesive quantity or the doses may be varied in accordance with the requirements for the different appliances of the set. The appliances may, in certain embodiments, be provided pre-attached, one to each holder. Preferably, the appliances are provided physically separate from the substrate bearing the adhesive, and may be provided on holders that are separate or detachable from the substrate bearing the adhesive. The appliances, where provided, are also preferably individually wrapped in their own sanitary containers and are positioned and oriented in their packages for easy pickup by the practitioner.

The system of the preferred embodiment of the invention is further provided with a sealant in a quantity suitable for preparing the teeth on which appliances are to be applied by the adhesive on the substrate. Single or multiple part sealers may be used, and each part is provided in a separate container either affixed to or separate from the substrate, along with such brushes or other applicators as may be convenient.

In certain preferred embodiments of the invention, each of the doses of adhesive is deposited onto the surface of the substrate in a strip that is narrower than the, width of an appliance base or tool edge that will come contact the substrate surface to scoop up the adhesive dose. Each strip of adhesive on the substrate is of a volume that is nominally the minimum required to effectively bond an appliance to a tooth. In addition, separate measured supplemental amounts, preferably one or two in number, each equal to about one tenth of the nominal volume, are deposited on each transfer area of the substrate surface in line with, but separated from, the main nominal adhesive dose. This allows the clinician the option of increasing the nominal main dose by ten or twenty percent on an appliance-by-appliance basis.

In certain preferred embodiments of the invention, a single dose adhesive such as typical light curable adhesives may be used and deposited on the transfer areas of the substrate surface in a contiguous strip. In alternative embodiments, multiple part adhesives may be deposited on the transfer areas of the substrate surface in separate fragmentary amounts such as in dot arrays, for example, by printing spots of each component in interleaved arrays on the substrate surface, in a pattern that lies in a line that is of a width less than the width of an appliance in contact with the substrate surface.

In the preferred embodiment of the invention, the substrate is formed in multiple layers, including an inner core of a thickness of a resilient foam material covered by a film of polyethylene or comparable non-stick flexible material. The cover is preferably also formed of multiple layers, preferably including a polymer layer and a foil layer.

In use, the doctor first opens and applies the sealant to the tooth of a patient. Then, the doctor removes the cover from a substrate on which the dose or doses of adhesive needed for treatment are deposited, exposing the adhesive. The appliance is then picked up, preferably from a holder attached to the substrate carrying the adhesive which holds a specific appliance for installation on a specific tooth of a patient. The appliance so picked up, for example, with tweezers or special tool, is scraped along the pattern of adhesive in one of the transfer areas of the substrate surface, causing the adhesive deposited on the transfer area of the surface to be cleanly removed from the substrate surface and transferred onto the base of the appliance. With a single part adhesive, the appliance is placed on the tooth and, if appropriate, the adhesive is light cured. With the multiple part adhesive, the scraping and removal of the adhesive from the substrate surface causes the separate amounts of the different parts of the adhesive to be thoroughly mixed together so that, upon application onto the surface of the tooth, the adhesive is sufficiently mixed to properly chemically cure.

The delivery system and method of the present invention provides the advantage that orthodontic adhesive, even though not pre-dispensed, can be easily picked up directly by the appliance. Further, the adhesive can be picked up by the appliance in a quantity that is either predetermined at, or that can be adjusted about, a nominal adhesive volume. As a result, the clinician is provided with control over the quantity of adhesive required in varying clinical situations, minimizing cleanup due to excess or minimizing the need for rebonding due to failure from inadequate adhesive.

With the delivery system of the present invention, the adhesive is not attached to the appliance or associated with its package; and thus, the shelf life of the adhesive does not impose a shelf life on the substantially more expensive appliance. The adhesive system of the present invention presents a low cost package of single dose adhesives in a form that can be disposed of separate from the appliances when an adhesive expiration date is reached. Further, the adhesive package, according to preferred embodiments the present invention, is inexpensive and occupies very little space in shipping or in the office of the practitioner.

The preferred embodiments of the invention further provide the advantages of single dose adhesive units, one for each appliance required to treat a single patient, and in a package by which all individual dose units can be opened at once, with minimal handling by the doctor or staff. In certain embodiments of the invention, adhesive primer is provided in a disposable, no-mix, non-light cure form. Further, certain embodiments of the invention provide adhesive light cure as well as multiple part chemical cure compositions. In additional embodiments, individual appliances are packaged in association with each of the single adhesive doses, which may vary in size from appliance-to-appliance.

These and other objectives and advantages of the present invention will be more readily apparent from the following detailed description of the drawings of the preferred embodiment of the invention, in which:

DETAILED DESCRIPTION OF THE DRAWINGS

The dental adhesive delivery system of the present invention is illustrated and described in several embodiments, including particularly embodiments for delivery of orthodontic adhesives. The dental adhesive delivery system of the invention, however, has utility in other dental applications, such as the bonding of bridges, crowns and other restorations and for other situations where a dentist can benefit from the convenient delivery of dental adhesive in predetermined or pre-measured quantities that are entirely consumed in a given treatment step. In orthodontics, for example, the delivery system of the invention provides orthodontic adhesive in a plurality of individual doses, each of which is of the quantity appropriate for the bonding of a single orthodontic bracket, for example, to a tooth. The adhesive delivery system of the invention may include the adhesive doses and their specially configured packaging, provided alone or in combination with a dental object, material or appliance which the individual doses of adhesive are configured to bond to a tooth or otherwise in the treatment of a dental patient.

Figure 1:
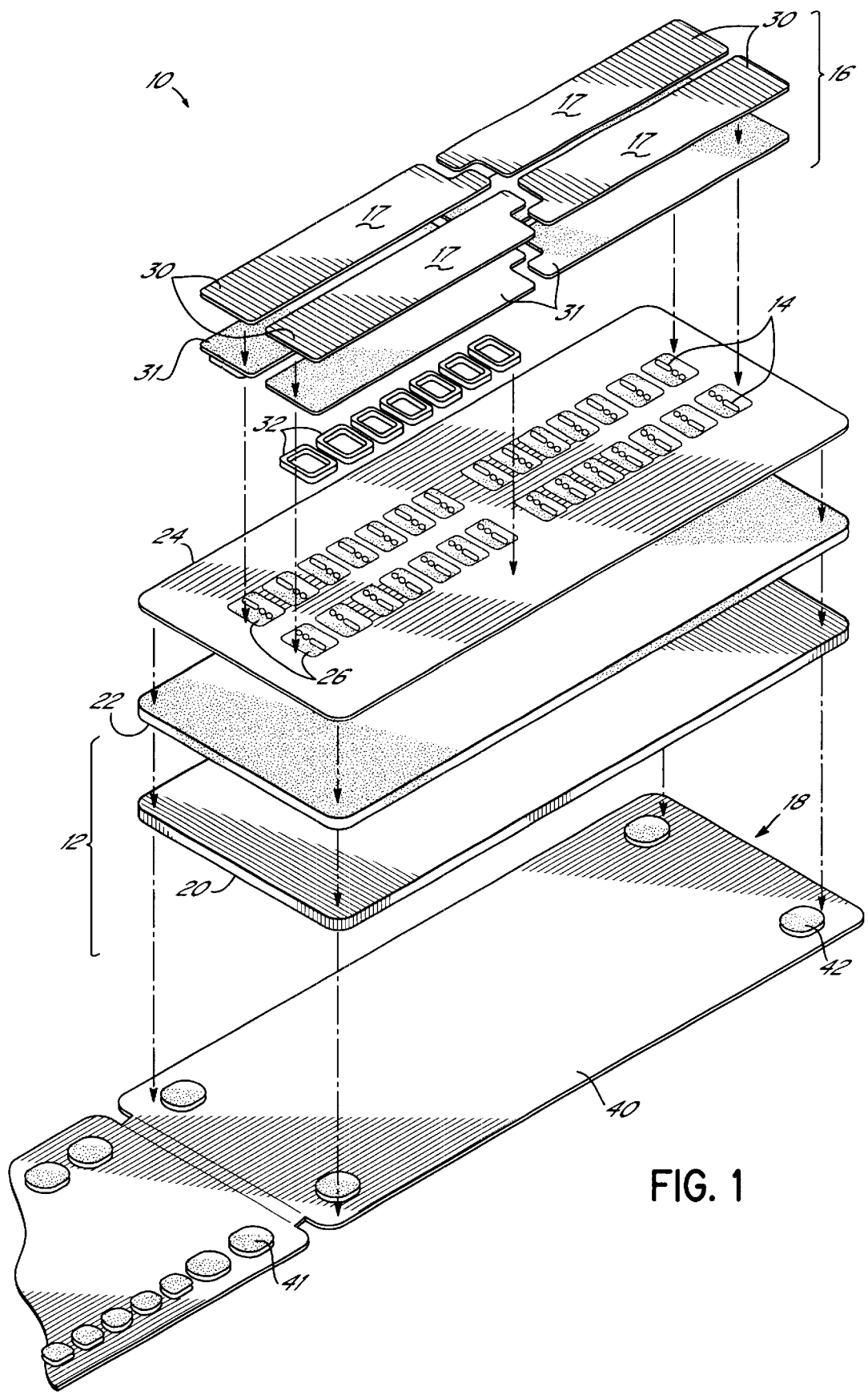
FIG. 1 is a disassembled isometric view of an orthodontic adhesive delivery system according to one embodiment of the invention.

One embodiment of the dental adhesive delivery system of the invention is the orthodontic adhesive delivery system 10 illustrated in part in FIG. 1. The system 10 of FIG. 1 is configured to provide orthodontic adhesive in individual appliance doses. The system 10 includes a substrate assembly 12, single dose amounts of orthodontic bracket bonding adhesive 14 supported on the substrate assembly 12, and a cover and seal 16 assembly enclosing one or more adhesive-containing cavities over the substrate assembly 12. In addition, the system 10 may include or have provision for outer packaging and mounting structure 18.

Figures 6A, 6B:
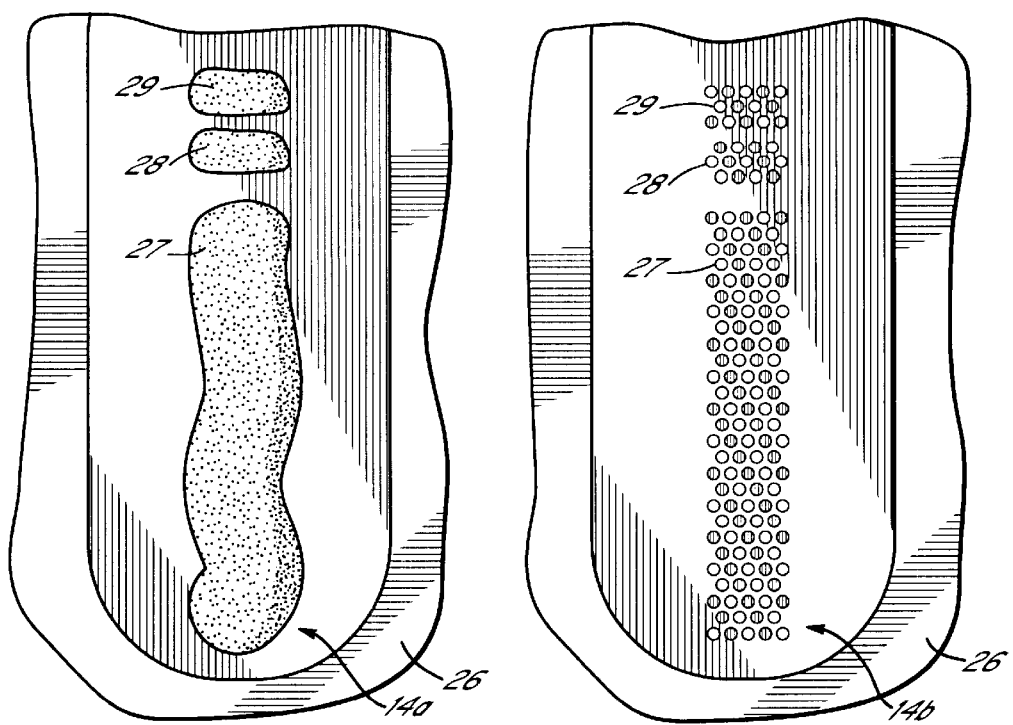
FIG. 6A is a plan view illustrating a dose of adhesive of the single part type on a transfer area of the surface of the substrate of the system of FIGS. 1 or 2.
FIG. 6B is a plan view, similar to FIG. 6A, illustrating a dose of adhesive of the two part type on a transfer area of the surface of the substrate of the system of FIGS. 1 or 2.
Figure 7A:
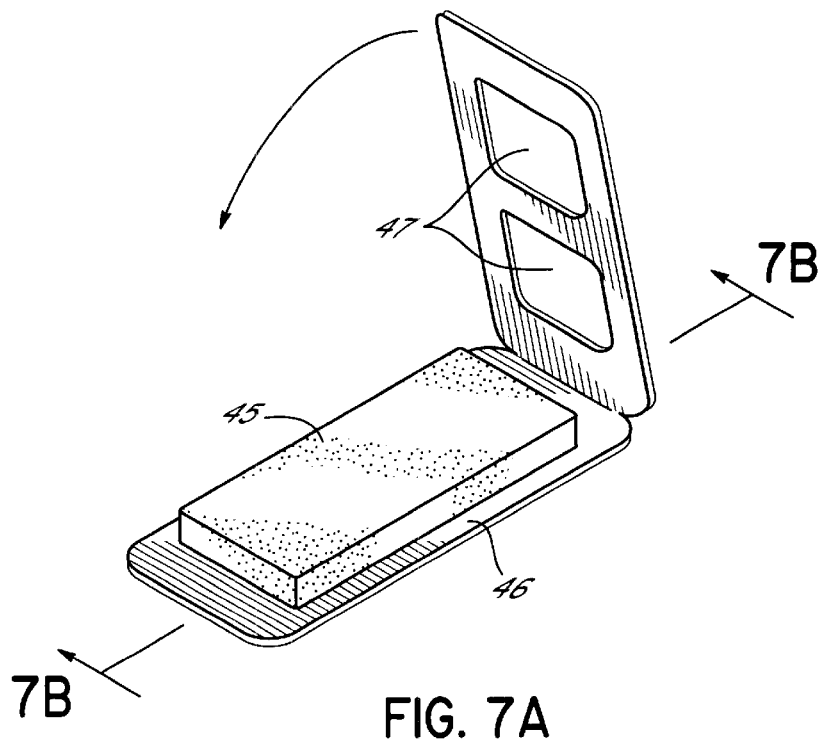
FIG. 7A is a perspective view of a sealant package portion of the system embodiment of FIG. 2.
Figure 7B:
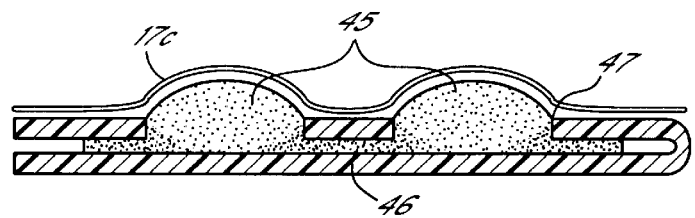
FIG. 7B is a cross-sectional view of the sealant package portion of FIG. 7A.
Figure 6C:
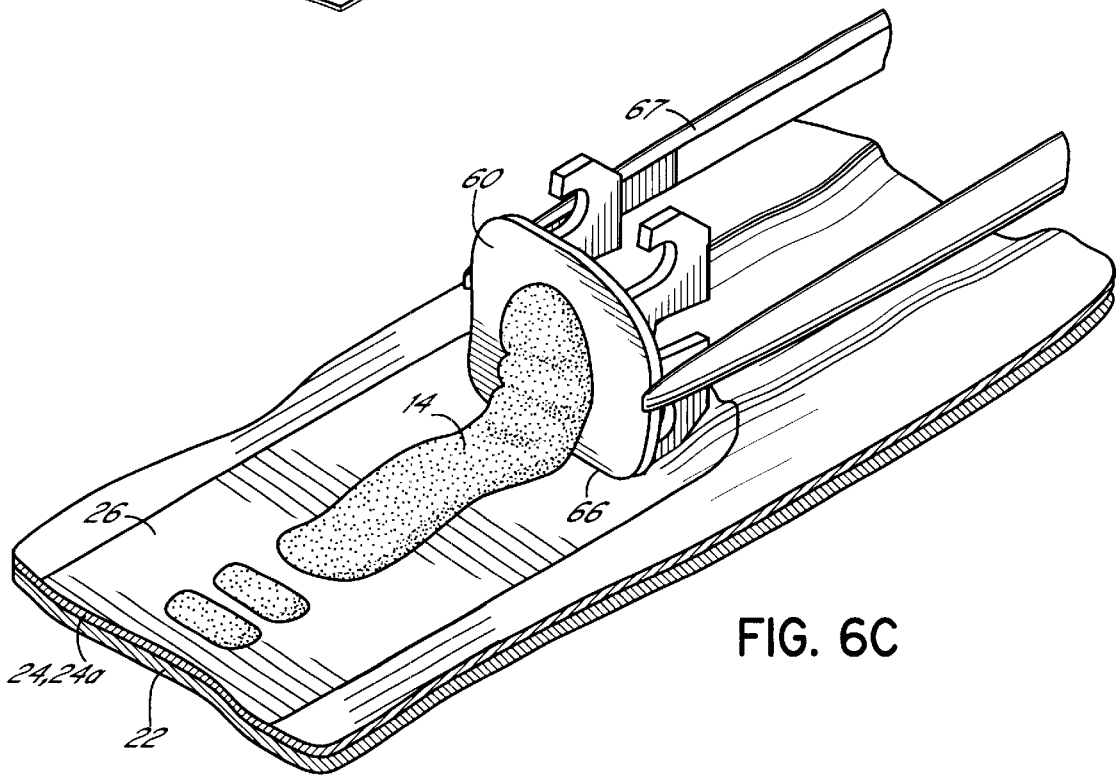
FIG. 6C illustrates the scooping of the adhesive from the substrate with the base of an appliance and the transfer of adhesive from the substrate to the base.

The substrate assembly 12, which is sometimes referred to herein as simply the substrate, is formed of three layers, including a backing or base layer 20 of sheet material, an inner layer 22 of compliant or compressible material, and an adhesive supporting surface layer 24 of a relatively non-stick, relatively flexible, and relatively adhesive impervious material. The base layer 20 may be a paper or cardboard layer, a layer of PVC or other plastic, or another material that will give the substrate 12 a degree of stiffness and flatness. The backing or base layer 20 is, for most such materials, preferably approximately 20–25 mils (0.02–0.025 inches or approximately 0.5–0.6 millimeter) in thickness. The inner compliant or compressible layer 22 is formed preferably of a polymeric foam material, preferably also approximately 20–25 mils thick. The surface layer 24 is preferably formed of a material such as polyethylene film, or other plastic or foil material, approximately 2–3 mils (approximately 0.56–0.08 mm) in thickness. The surface layer 24 is flexible and sufficiently slippery to allow the edge of an orthodontic appliance or of a tool, which edge is not necessarily straight and is typically slightly convex, to easily slide over the surface of the substrate. The inner core layer 22 is compressible, being designed to be deformed by the non-straight and typically convex edge of a bracket base or pad or of a dental tool as it is slid over the surface or film layer 24 of the substrate 12 so that the substrate 12 as a whole is compliant and conforms to the shape of the perimeter of the base of the appliance or tool. The combination of the core layer 22 and the surface layer 24 may, but need not, be resilient so as to return at least partially to its undeformed shape after being deformed by the appliance or tool edge. The compliance with the sliding edge of appliance base or tool allows the edge to cleanly scoop up and wipe the adhesive from the surface 12 as the edge is slid over the surface layer 24 of the substrate 12. As shown in FIG. 6C, an orthodontic appliance in the form of an orthodontic bracket 60 is being held with tweezers 67 and its convex edge 66 is used to cleanly scoop up the adhesive dose 14 on a transfer area 26 of a substrate 12 by pressing the convex appliance edge 66 against the surface layer 24 of the substrate 12 as the core 22 is compressed.

The surface of the substrate 12 has a plurality of adhesive supporting and transfer areas 26 at which the slippery film layer 24 is exposed. The film layer 24 may be colored a dark color or may be clear in the transfer areas 26 to expose the inner foam layer 22, which is then black or a dark color. This coloration allows the adhesive 14, which is typically light colored opaque or translucent, to be clearly visible against the dark background of the surface of the substrate 12 at the areas 26. In manufacture, the layers 20, 22 and 24 are permanently laminated together and the periphery of the substrate 12 is then die cut to the final shape of the substrate 12, which is, for example, rectangular and approximately 2–3 inches in width to 5–7 inches in length.

Once the substrate 12 is formed, a single dose of orthodontic appliance adhesive 14 is deposited onto each of the transfer areas 26 on the surface 24 of the substrate 12. An orthodontic adhesive is, for example, a Bisphenol A-Glycidyl Methacrylate type adhesive having a low vapor pressure. The adhesive is typically a paste containing a glass fiber or other filler material and has a consistency resembling that of modeling clay. Such an adhesive is typically catalyzed by a free radical mechanism. Both light cure and chemical cure adhesives are suitable for the individual doses of the adhesive 14. Such adhesives are preferably dispensed in one line 27 of adhesive, followed by two short lines or dots 28, 29 of the adhesive. The line 27 of adhesive may be premeasured to a standard minimum dose for the appliance, with the dots 28, 29 being of quantities each equal to about ten percent of the minimum dose of the line 27, as better illustrated in FIGS. 6A and 6B. The line 27 and dots 28, 29 are, for example, about 10–15 mils in width and height. The provision of the adhesive doses 14 in a pre-measured minimum amount as the line quantity 27 with the additional dots 28, 29 of 10% additional amounts allows the orthodontist to pick up either only the line quantity 27, which provides a predetermined nominal minimum amount of adhesive which is not too much for any appliance, or to pick up an additional ten or twenty percent more than the nominal amount by picking up one or both of the dot quantities 28, 29, as the orthodontist deems most clinically advantageous. Different numbers or sizes of additional dots 28, 29 or supplemental amounts of adhesive may be provided in combination with various sizes of a line quantity 27 for different ones of the individual doses 14 in order to deliver a proper predetermined nominal for each of the different appliances of a set. In addition, systems 10 can be provided in different dose sizes to provide a range of options for the dentist or orthodontist based on the preferences or techniques of the practitioner or the differing requirements for individual patents.

Light cure or UV adhesive is one typical adhesive for orthodontic applications as well as for other dental applications. Such adhesive, which is normally a single part adhesive, is provided in the system 10 dispensed onto the transfer areas 26 of the substrate 12 as a homogeneous bead that needs no mixing prior to use. Such a homogeneous bead is illustrated as bead 14a in FIG. 6A. Chemical cure adhesive is also used for securing orthodontic brackets to teeth and for many other dental uses. Chemical cure adhesives are often provided as two part adhesives that cure upon the mixing of the two parts. Such adhesives may be used in the system 10 dispensed on the substrate layer 24 as an array of separate component dots, illustrated as A dots and B dots in FIG. 6B. With the two part chemical cure adhesive provided on the substrate, the shear and rolling of the dots as they are scooped by the edge of an orthodontic appliance 60, as illustrated in FIG. 6C, mixes the two different dot components. Furthermore, as the chemical cure adhesive components are squeezed between the appliance base and the surface of a tooth as the appliance is applied to the tooth, additional mixing of dots A and B occurs. In addition, chemical cure adhesive will pick up residual catalyst from a primer-sealant that has been applied by the orthodontist to the surface of the patient's tooth before mounting the bracket, further enhancing the curing of the adhesive. Diffusion gradients exist all through the mixing and application processes, contributing to the mixing of the A and B components and to the distribution of catalyst, thereby affecting the cure of the adhesive without more manual mixing than described above.

Around each of the individual adhesive dose transfer areas 26, a seal may be formed between the cover 16 and the substrate 12 that is effective to stop the loss of any volatile components of the adhesive and to provide sufficient darkness to insure that no premature light curing or light-induced degradation of the adhesive takes place during the required shelf life of the product. In the embodiment of FIG. 1, the cover 16 includes a foil layer 30, a polymer layer 31 and a foam layer 32. The foil layer may be, for example, a 2 mil thick layer of aluminum foil, which will fold sharply at the beginning of each successive foam seal 32 to keep the seal out of the way of the operator while appliance adhesive is being accessed. The polymer layer may be, for example, a 0.5 mil thick layer of polyethylene film effective to prevent contamination of the adhesive by the foil and to provide a non-stick surface to present to the adhesive in the event that it does touch the seal.

The foam layer 32 may be in the form of a set of rectangular windows, each formed of a 20–25 mil thick polyethylene foam and bonded to the polymer layer 31 so as to surround the perimeter of each of the transfer areas 26 when the cover 12 is situated over the substrate 12. The lower surface of the foam layer 32 is coated with pressure sensitive adhesive having properties that provide a bond between the foam layer 32 of the cover 16 and the substrate 12 that is weaker than the bond between foam layer 32 and the polymer layer 31 of the cover 16 The individual window like components of the foam layer 32 on the cover 16 each individually surround the periphery of one of the transfer areas 26. The foam layer 32 is of a thickness that prevents the cover from contacting the adhesive doses 14 on the surface 24 of the substrate 12.

The cover 16 may be formed in one or more parts 17, which are shown as four parts 17 in number in the drawings, with each part 17 covering seven of the individual adhesive doses of adhesive 14 associated with each tooth of one of the four upper or lower, right or left half arches of a patient. These parts 17 are preferably formed by die cutting the cover 16 after the three layers 30–32 are laminated together. The four parts 17 of the cover 16 are placed on the substrate 12 with release tabs 33 arranged to allow random opening of any one of the parts 17.

The system 10 embodiment of FIG. 1 is also provided with an outer packaging component 40 which carries printed information and graphics and supports adhesive holders 41 for the mounting of appliances to be installed on the patient with the adhesive doses 14 as well as adhesive mounting feet 42 for enabling the fixing of the substrate 12 to the tray or other structure to hold it in place during use. The packaging layer 40 may be fabricated from metallized MYLAR of, for example, about 2 mils in thickness. The non-foil side of the packaging layer 40 faces outwardly and contains printing and graphics while the foil side has mounted thereto a plurality of adhesive mounting pads 41, one corresponding to each of the adhesive transfer areas 26, for supporting the appliance that is to be applied to a specific one of the teeth of a patient with the adhesive dose 14 supported on the surface 24 of the substrate 12 at the associated transfer area 26.

The pads 41 are arranged on the packaging layer 40 so as to contact the surface 24 of the substrate 12 when the packaging layer 40 is wrapped around the substrate 12. The side of the pad 31 away from the packaging layer 40 is coated with pressure sensitive adhesive that forms a stronger bond than adhesive joining the pads 41 to the packaging layer 40, so that the pads 41 transfer to and remain with the substrate 12 when the packaging layer 40 is removed. Similarly, the feet 42 are bonded to the packaging layer 40 so as to transfer to the bottom of the substrate 12 to form bonding feet to hold the substrate 12 to a work surface such as a tray or table.

The pads 41 are 10–15 mils thick and formed of white polyethylene double-sided, self-adhesive foam to stand out against a darker background of the fundamental substrate 12. Each pad is preferably shaped to look like the en-face view of the crown of a specific tooth of a patient to visually synchronize not only with the tooth to which an appliance is to be bonded, but to correspond in shape with that of the base of a corresponding appliance such as those described in commonly assigned U.S. Pat. No. 5,993,206 by an inventor hereof, hereby expressly incorporated by reference herein. The feet are about 5 mils in thickness, also formed of self-adhesive, double-sided polyethylene.

Figure 2:
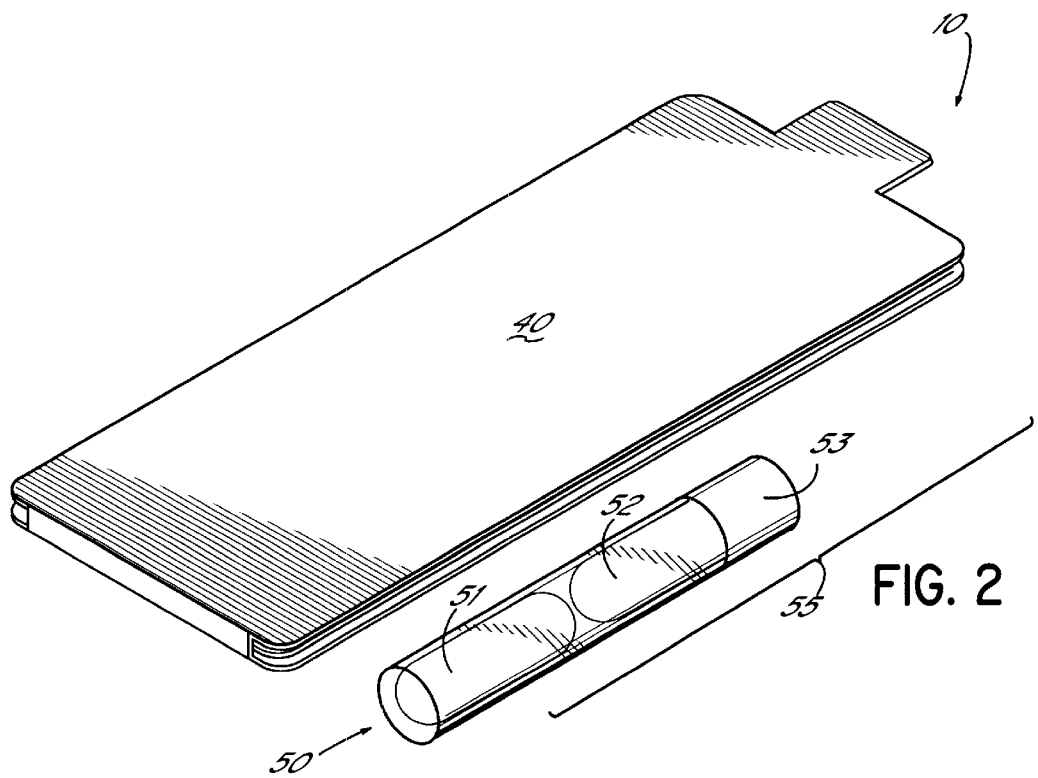
FIG. 2 is an assembled isometric view of an orthodontic adhesive delivery system according to one preferred embodiment of the invention incorporating the embodiment of FIG. 1 in a form packaged for shipping or storage.
Figure 3:
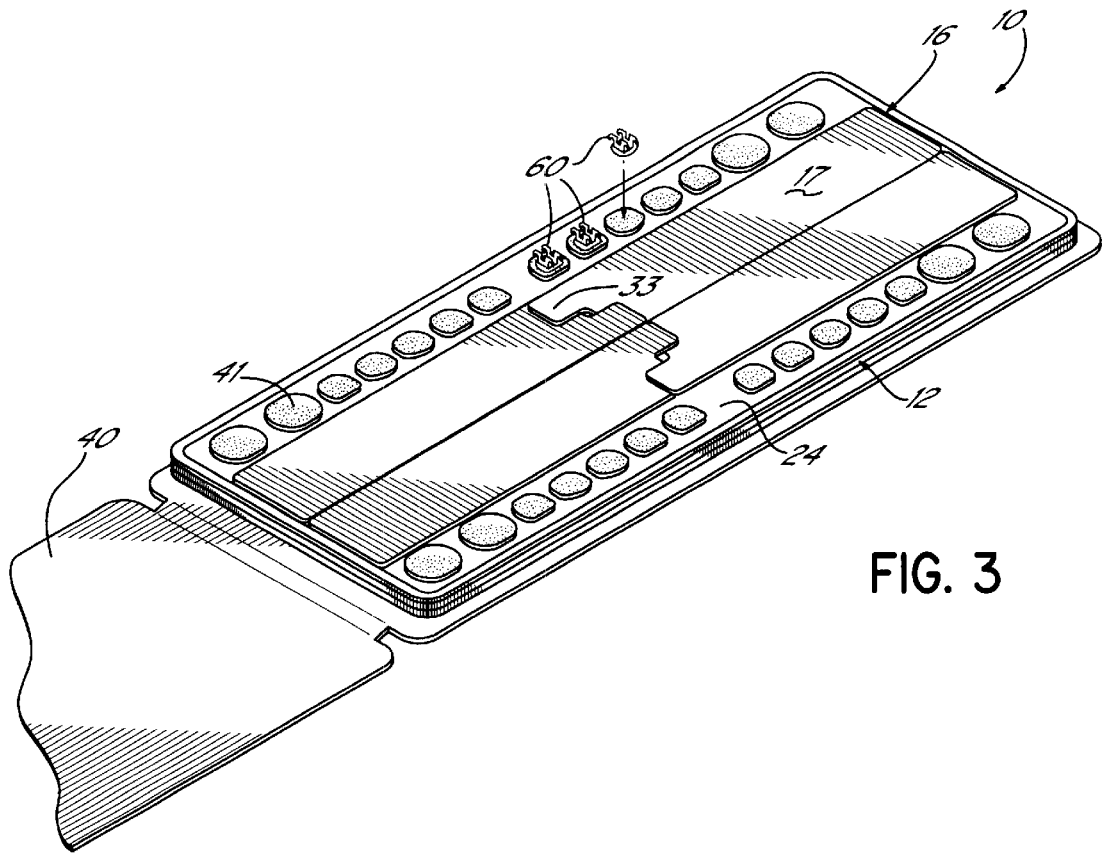
FIG. 3 is an isometric view, similar to FIG. 2, of an orthodontic adhesive delivery system of the embodiment of FIG. 1 prepared for use.

The packaging layer 40 is shown in FIG. 2 in a closed condition around a substrate 12, and is shown in FIG. 3 in an opened condition exposing the cover 16 sealed onto the substrate 12 and the appliance holder pads 41 transferred and affixed to the outer edges of surface layer 24 of the substrate 12 so that one pad 41 is immediately adjacent to and associated with each one of the transfer areas 26 that carry a dose of adhesive 14 for the installation of an appliance that can be supported on the corresponding pad 41.

In the embodiment of the adhesive delivery system 10 of FIG. 1, there is preferably provided a supply of sealer-primer. Such supply may be, for example, an ampule 50 containing the sealer-primer for use by the orthodontist for the pre-coating of the teeth to which the adhesive doses 14 are to be applied for securing appliances to the teeth. The ampule 50 may contain two glass vials 51, 52, respectively, containing a resin and catalyst. Where two part chemical cure adhesive is being used as illustrated in FIG. 6B, the same resin and catalysts would be used as in the A and B type two part chemical curing adhesive 14b, but having a lower viscosity and molecular weight, with no glass filler material, whereby it is more flowable than such an adhesive. The primer contains a fast drying solvent to lower the viscosity of the sealer-primer and to, by evaporation, limit the thickness of the primer left on the tooth. The ampule 50 also has, at one end thereof, a wick 53. Crushing of the ampule 50 breaks the vials 51, 52 within the ampule 50 and allows the two A and B parts of the sealer-primer to mix and wet the wick 53. With the wick 53, the mixed sealer-primer can be transferred to, the surface of a tooth, where it wets the etched surface of the tooth on which it is applied, and achieves a chemical bond with the bracket adhesive 14 when the adhesive coated appliance is placed on the tooth. The system 10 along with the ampule 50 constitute a complete appliance application kit 55.

When the system 10 is uncovered for use by an orthodontist or assistant, as illustrated in FIG. 3, orthodontic appliances may be assembled onto each of the pads 41. The unique appliance designed for a specific tooth of a patient is associated with specific doses of adhesive 14 on one of the transfer areas 26, and placed on the pad 41 adjacent the transfer area 26 carrying the associated adhesive dose 14. The doses 14 may be all the same size or may be of different doses of custom pre-measured amounts appropriate for and specifically suitable for the associated bracket for which the dose is intended to be used. Illustrated are orthodontic brackets 60 for an upper right central and upper right lateral secured to their respective associated pads 41 with a bracket for an upper right central positioned to be secured to its associated pad 41. Such appliances 60 may be applied to the pads 41 at the orthodontist's office, or may be pre-applied by the appliance manufacturing or supplying company and delivered to the orthodontist as a complete assembled appliance installation package of appliances 60 and either a system 10 or a kit 55 that may include a system 10 along with a sealer-primer ampule 50.

Figure 4:
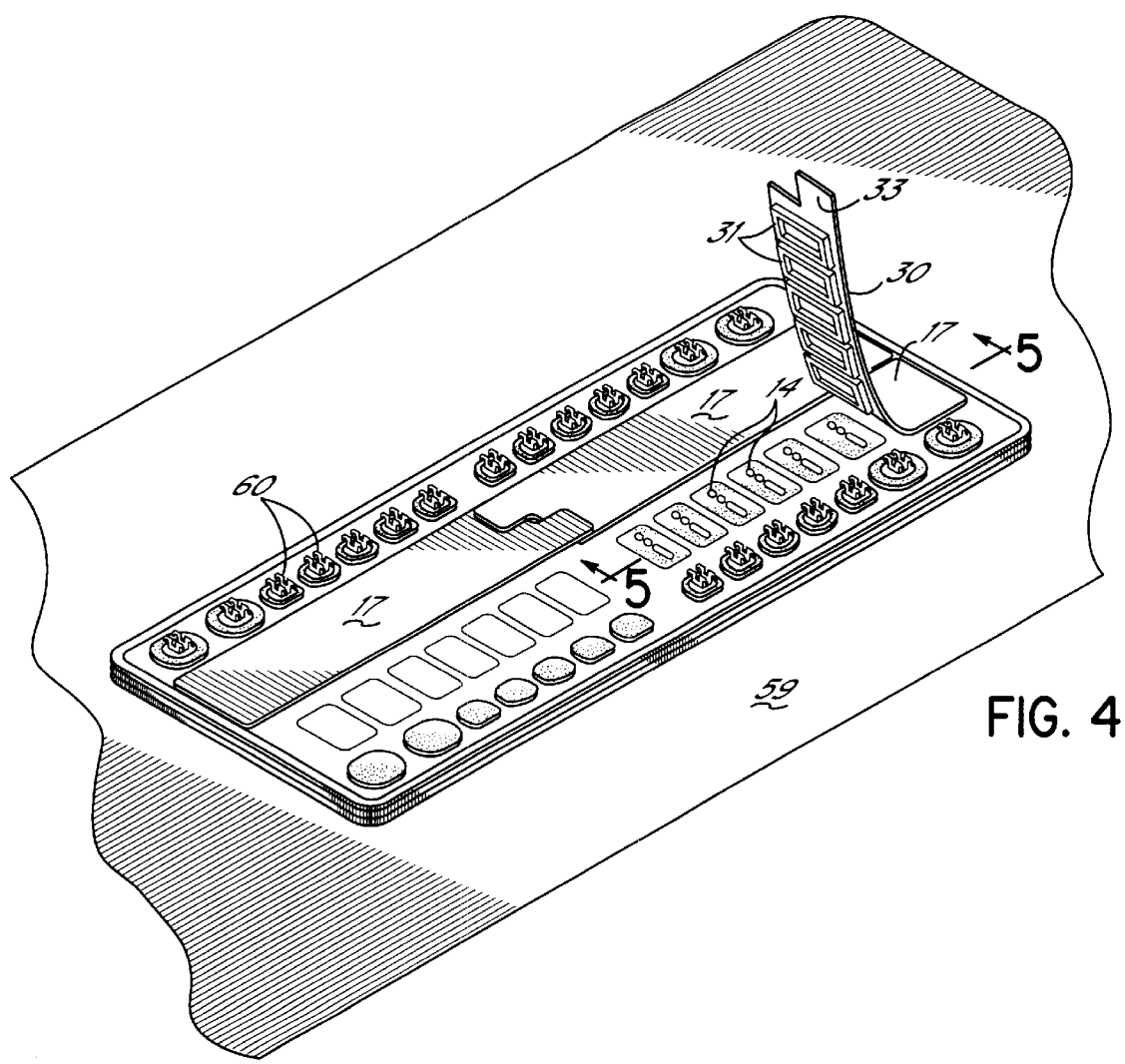
FIG. 4 is an isometric view, similar to FIG. 3, of an orthodontic adhesive delivery system of the embodiment of FIG. 1 in use.
Figure 5:
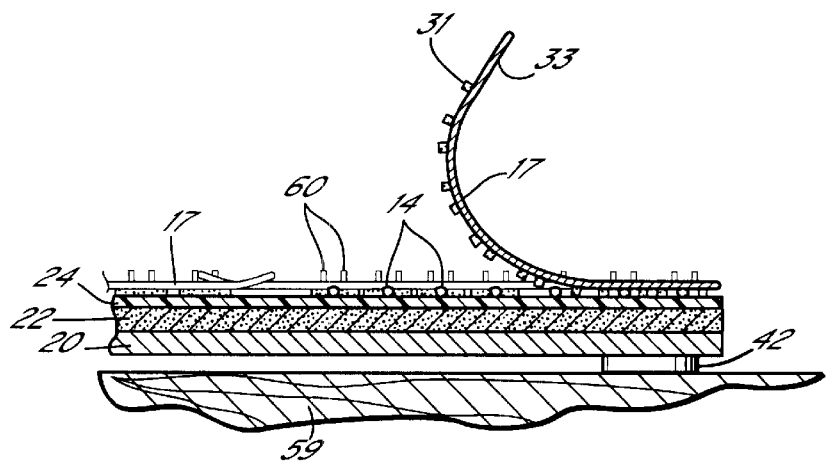
FIG. 5 is a cross-sectional view taken along the line 5—5 of FIG. 4.

Use of the system 10 is illustrated in FIGS. 4 and 5, which show a system 10 mounted on a table or tray 59 as might be adjacent a chair in an orthodontist's office, with one of the parts 17 of the cover 16 being opened. In the drawings, the adhesive 14 and appliances 60 for the lower right arch of the patient have already been applied, with the part 17 of the cover 12 being removed to expose the adhesive 14 for the lower left arch of the patient.

Figure 1A:
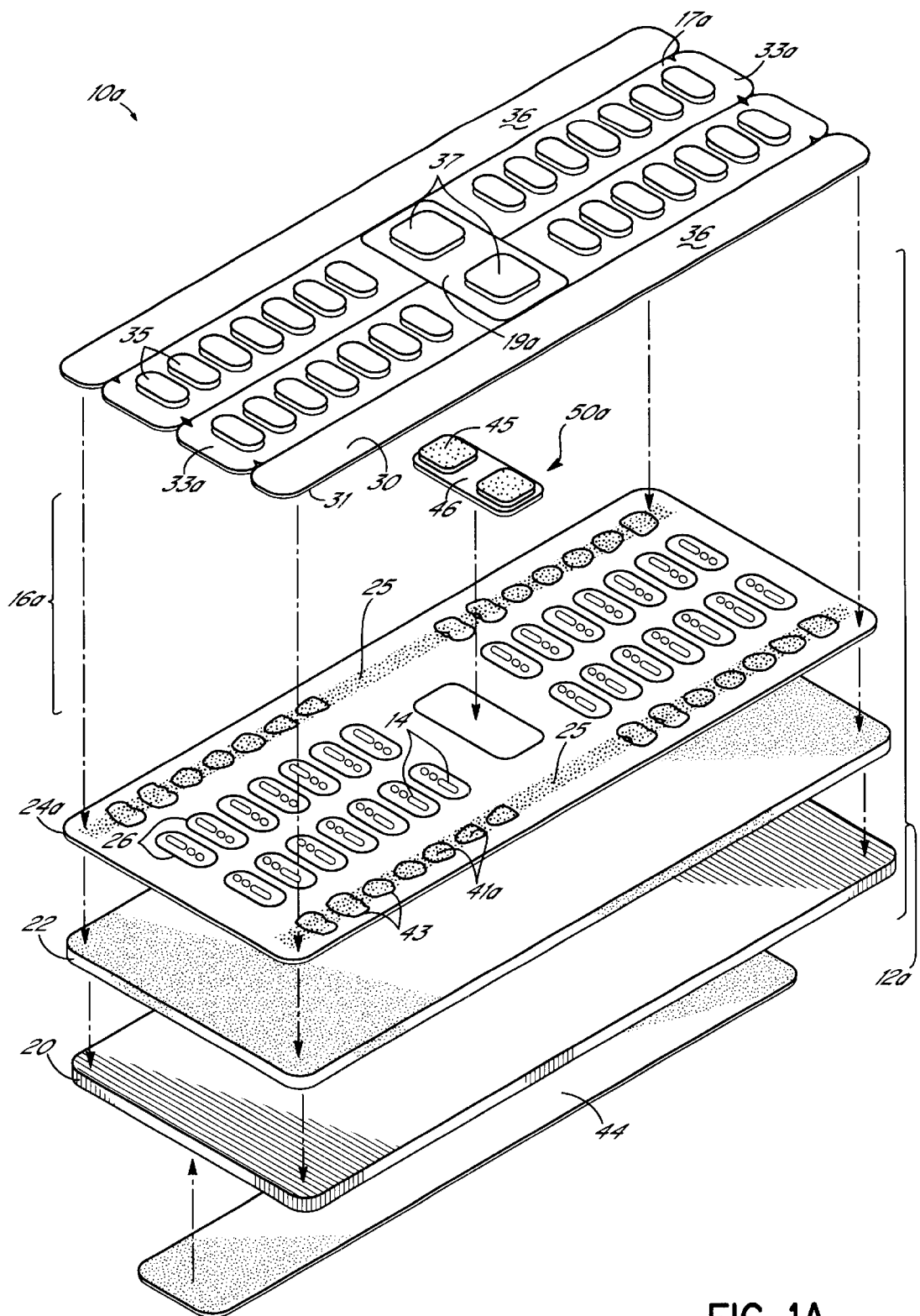
FIG. 1A is a disassembled isometric view, similar to FIG. 1, of an orthodontic adhesive delivery system according to another embodiment of the invention.

An alternative embodiment to the system 10 described above is adhesive delivery system 10a illustrated in FIG. 1A. System 10a as illustrated has three primary components, which include a substrate assembly 12a, the single dose amounts of bracket bonding adhesive 14 and an adhesive cavity cover and seal 16a. Outer packaging is not necessary or may include simply a sleeve or envelope (not shown) to contain the system 10a and bear printed information and graphics.

The substrate assembly 12a, is formed of the bottom and core layers 20, 22 and of top layer 24a as in the case of the substrate 12 of system 10 described above. The surface layer 24a of the substrate 12a has the plurality of adhesive supporting and transfer areas 26 on each of which one of the single doses adhesive 14 is applied of either the single part light curable type or the two part chemical curable type as illustrated in FIGS. 6A and 6B. Appliance holder positions 41a are formed directly on the surface layer 24a by preprinted outlines profiles 43 of each of a patient's teeth covered by strips 25 of pressure sensitive adhesive dispensed onto the layer 24a over the printed tooth outlines 43. The outlines 43 of the holder positions 41a are printed on the surface layer 24a oriented 90° to the orientations of the pads 41 in the embodiment described above so that the appliances 60, when positioned and oriented on the outlines 43 as they would be when properly located on the corresponding tooth of the patient, are positioned for easy pickup by the orthodontist with the use of tweezers.

In the embodiment of FIG. 1A, a cover 16a, provided to form a seal with the surface 24a of substrate 12a around each of the transfer areas 26, differs from the cover 16 described above. The cover 16a includes the foil layer 30 and polymer layer 31, but, instead of foam layer 32, the cover 16a is deformed into single dose adhesive covering pockets 35 that are 20–25 mils deep to avoid contact with the adhesive doses 14 while permitting the side of cover 16a having polymer layer 31 thereon to directly contact and seal to the surface layer 24a of the substrate 12a. The foil layer 30 be a 2 mil thick layer of aluminum foil and the polymer layer may be a 0.5 mil thick layer of polyethylene film. The seal is formed around sets of the areas 26, for example, to include each quadrant. Alternatively, the seal may be formed around the entire set of individual doses to be used at one sitting, around sets of a plurality of doses for either the upper or lower arch of the patient, around other combinations of individual doses or around each dose individually.

The cover 16a is preferably die cut with score lines into four parts 17a, with each part 17a covering seven of the individual adhesive doses of adhesive 14 associated with each tooth of one of the four upper or lower, right or left half arches of a patient. The four parts 17 of the cover 16 are placed on the substrate 12 with release tabs 33 arranged to allow random opening of any one of the parts 17. Edge strips 36 are similarly die cut from the cover 16a to provide separately removable covers for the adhesive strips 25.

The substrate 12a of system 10a is provided with an adhesive base 42a to permit the bottom of the substrate 12a to be removably attached to and held in position on an orthodontist's tray. The adhesive base 42a is covered with a removable strip of silicone treated paper 44.

In the embodiment of FIGS. 1A–5A, there is provided a pouch 50a containing sealer-primer for the pre-coating of the teeth to which the adhesive doses 14 are to be applied for securing appliances to the teeth. The pouch 50 contains a core 45 of polyurethane foam or other absorbent carrier material, which may be in one or more pieces to contain a one part sealer-primer, or which may be formed of at least two pieces to contain both parts of a two part sealer-primer, with one part containing the same resin used in the A and B type two part chemical curing adhesive (FIG. 6B) and the other part containing the catalyst of the two part adhesive.

Figure 2A:
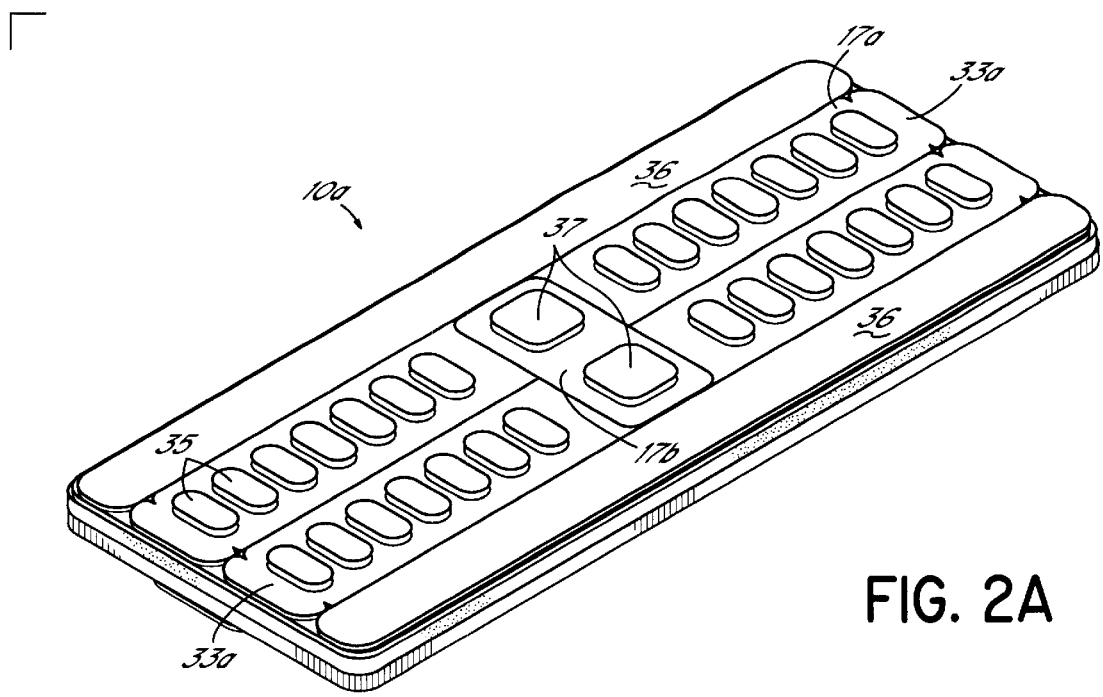
FIG. 2A is an assembled isometric view similar to FIG. 2 of an orthodontic adhesive delivery system according to the embodiment of FIG. 1A.

The pouch 50a may be formed by folding a plastic envelop 46 having a window 47 in one side thereof that is smaller than the dimensions of the foam core 45 so that the envelop 46, when folded over, traps the foam core 45 in a way that allows the foam core 45 to project outwardly from the window 47. A cover for the pouch 50a may be formed by die cutting an area 19a in the center of the cover 16a with one or more raised pockets 37 therein in the center thereof coinciding with the window 47. The envelop 46 with the core 45 assembled therein is then bonded to the center of the surface layer 24a of the substrate 12a and the cover 16a is sealed over the envelop 46 to the surface layer 24a of the substrate 12a, with the periphery of the area 19a sealed with releasable adhesive either to the surface layer 24a of the substrate 12a or to the envelop 46 around the core 45. Alternatively, in lieu of using the envelop 46, the core 45 may be bonded directly to the surface layer 24a of the substrate 12a. A fully assembled and sealed system 10a is illustrated in FIG. 2A.

Figure 4A:
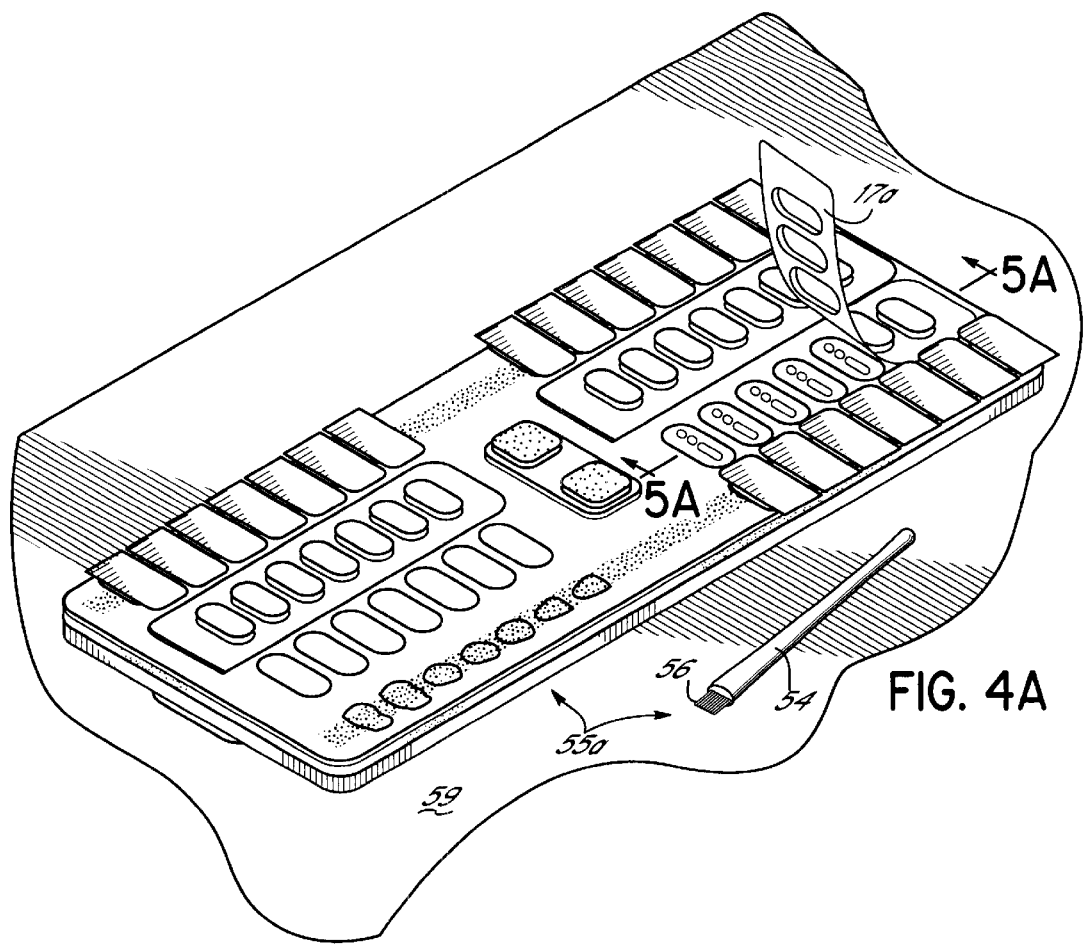
FIG. 4A is an isometric view, similar to FIG. 4, of an orthodontic adhesive delivery system of the embodiment of FIG. 1A in use.

A brush or applicator 54 is separately provided to form a kit 55a as illustrated in FIG. 4A. By dipping the tip 56 of the brush or applicator 55a against the exposed foam core 44, the sealer-primer can be transferred to the teeth.

Figure 3A:
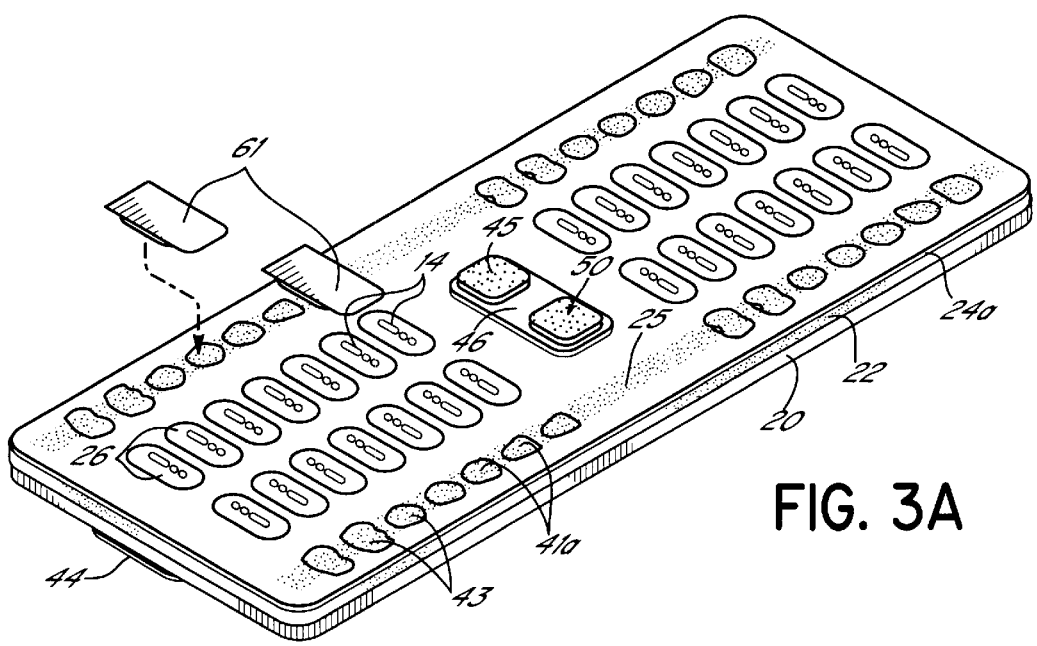
FIG. 3A is an isometric view, similar to FIG. 3, of an orthodontic adhesive delivery system of the embodiment of FIG. 1A prepared for use, and with individual prepackaged orthodontic appliances provided in association with the respective adhesive doses.

In lieu of mounting orthodontic appliances 60 directly to the substrate 12, 12a, the appliances 60 may be contained in individual packages 61. These packages 61 may be similar to blister packs of the type used to individually package pills, as illustrated in FIG. 3A. Such packages 61 can be adhered to the appliance support positions 41a on the surface layer 24a of the substrate 12a or on the supports 41 of the embodiment of the system 10 of FIGS. 1–5 described above. Alternatively, such packages can be made to snap into recesses in the substrate 12 as described in U.S. Pat. No. 5,354,199, hereby expressly incorporated by reference herein.

Figure 5A:
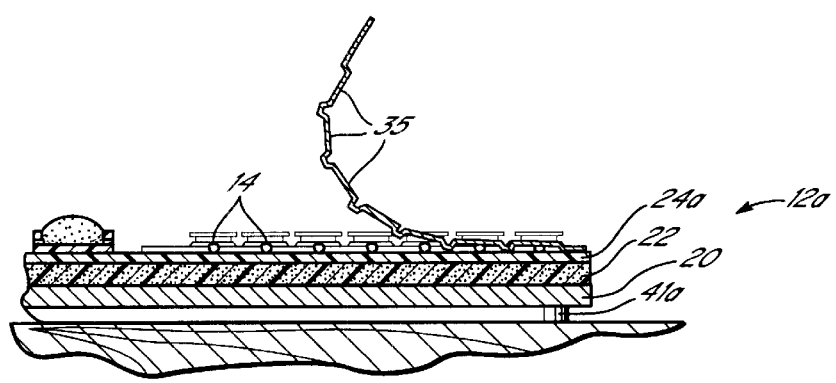
FIG. 5A is a cross-sectional view taken along the line 5A—5A of FIG. 4A.
Figure 4B:
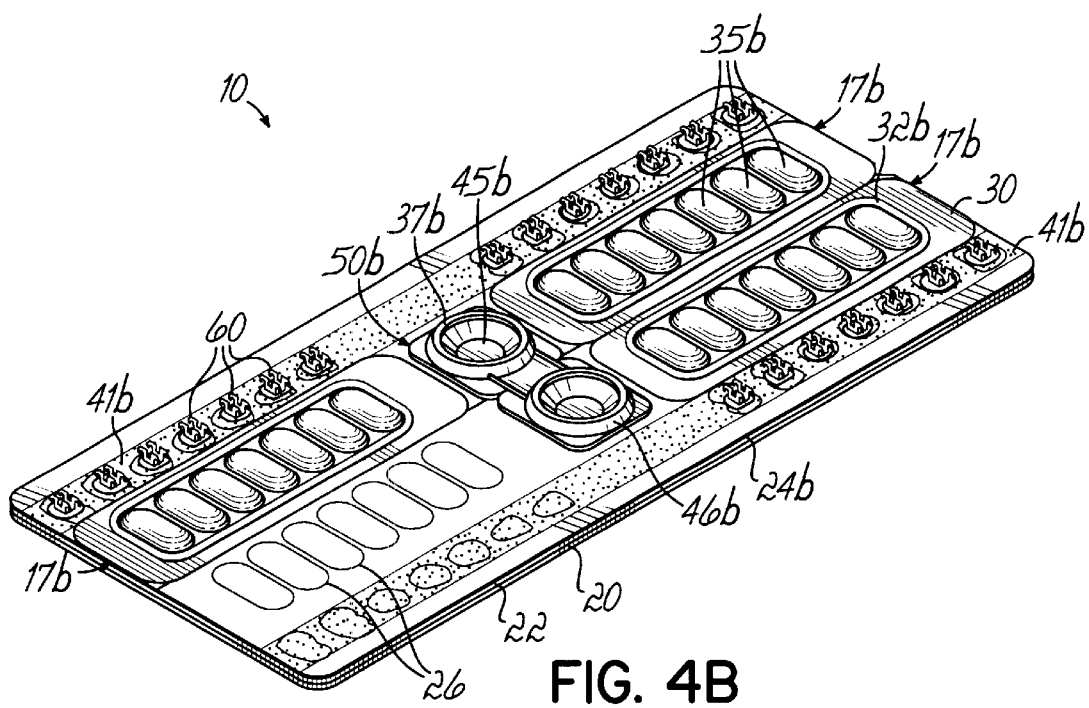
FIG. 4B is an isometric view, similar to FIGS. 4 and 4A, of an orthodontic adhesive delivery system of the embodiment of FIG. 1B in use.

Use of the system 10a is illustrated in FIGS. 4a and 5a, which show a system 10a mounted on a table or tray 59 adjacent a chair in an orthodontist's office, with one of the parts 17a of the cover 16a being opened. Use of the system 10a is similar to that described above for the embodiment of system 10.

Figure 1B:
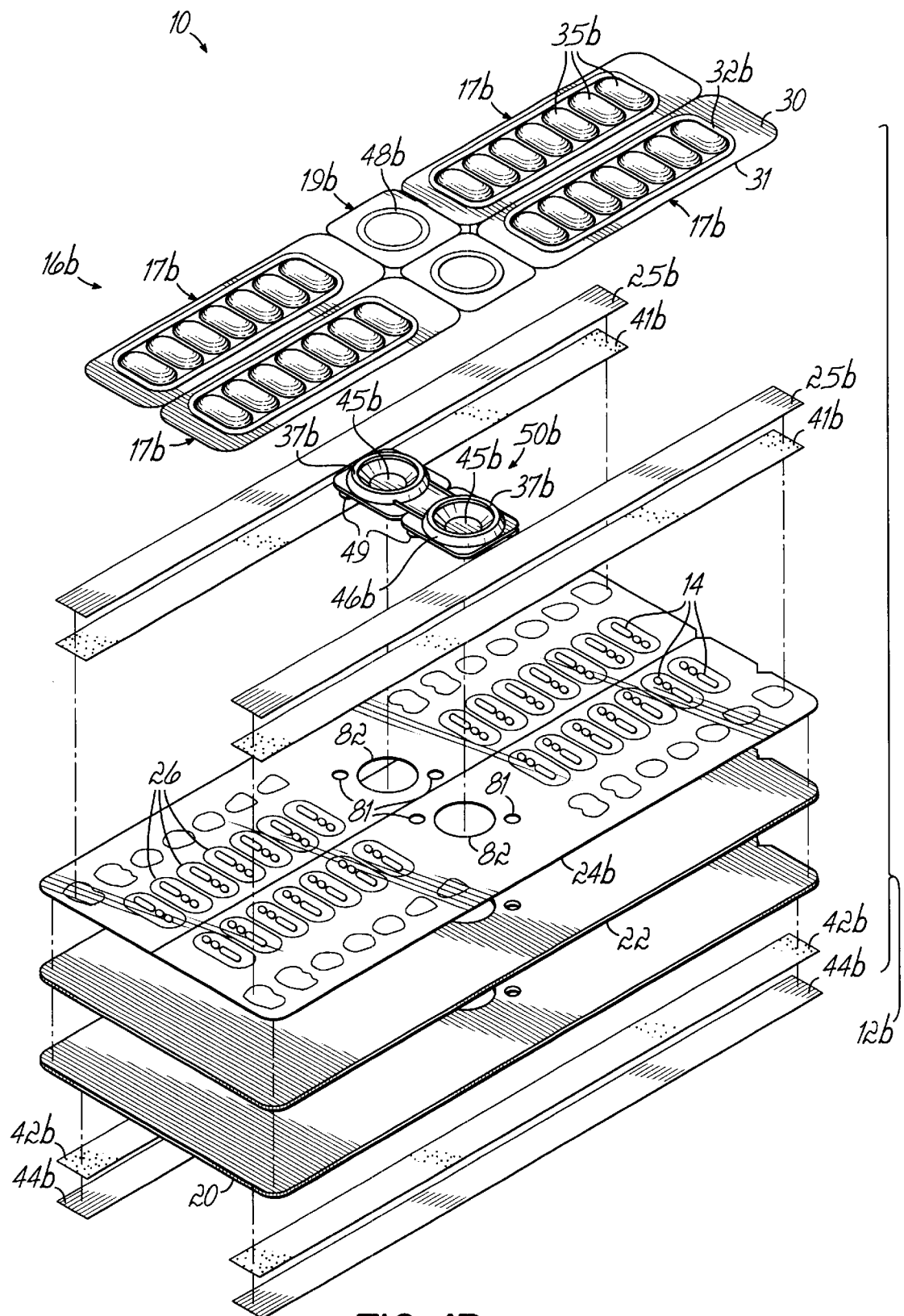
FIG. 1B is a disassembled isometric view, similar to FIGS. 1 and 1A, of an orthodontic adhesive delivery system according to a further embodiment of the invention.

A further alternative embodiment to the systems 10 and 10a described above is adhesive delivery system 10b illustrated in FIG. 1B. System 10b is illustrated as including substrate assembly 12b, the single dose amounts of bracket bonding adhesive 14 and an adhesive cavity cover and seal 16b. Outer packaging (not shown) may be provided as in systems 10 and 10a above.

The substrate assembly 12b is formed of bottom and core layers 20 and 22, described above, and of a top layer 24b similar to layer 24 or 24a described above. The surface layer 24b of the substrate 12b similarly has the plurality of adhesive supporting and transfer areas 26 on each of which one of the single doses adhesive 14 is applied of either the single part light curable type or the two part chemical curable type as illustrated in FIGS. 6A and 6B, respectively. Appliance holder pressure-sensitive adhesive is applied in strips 41b directly on the surface layer 24b, optionally over preprinted outlines or profiles of each of a patient's teeth (as profiles 43 in FIG. 1A above). The adhesive strips 41b are covered by strips 25b of silicone treated release paper.

In the embodiment of FIG. 1B, cover 16b, which is provided to form a seal with the surface layer 24b around each of the transfer areas 26, includes the foil layer 30 and polymer layer 31 deformed into single dose adhesive covering pockets 35b that are approximately 20–25 mils deep to avoid contact with the adhesive doses 14 while permitting the side of cover 16b to directly contact and seal to the surface layer 24b of the substrate 12b in a closed loop band 32b that encircles a set of adhesive doses 14 on areas 26, for example, that include one for each tooth of a quadrant. The cover 16b is die cut into four parts 17b, with each part 17b covering seven of the individual adhesive doses of adhesive 14 associated with each tooth of one of the four quadrants of a patient. The four parts 17b of the cover 16b are placed on the substrate 12b in an arrangement that allows random opening of any one of the four parts 17b.

The substrate 12b of system 10b are provided with adhesive strips 42b on the bottom thereof to permit the substrate 12b to be removably attached to and held in position on an orthodontist's tray. The adhesive strips 42b are covered with a removable strip of silicone treated release paper 44b.

Figure 2B:
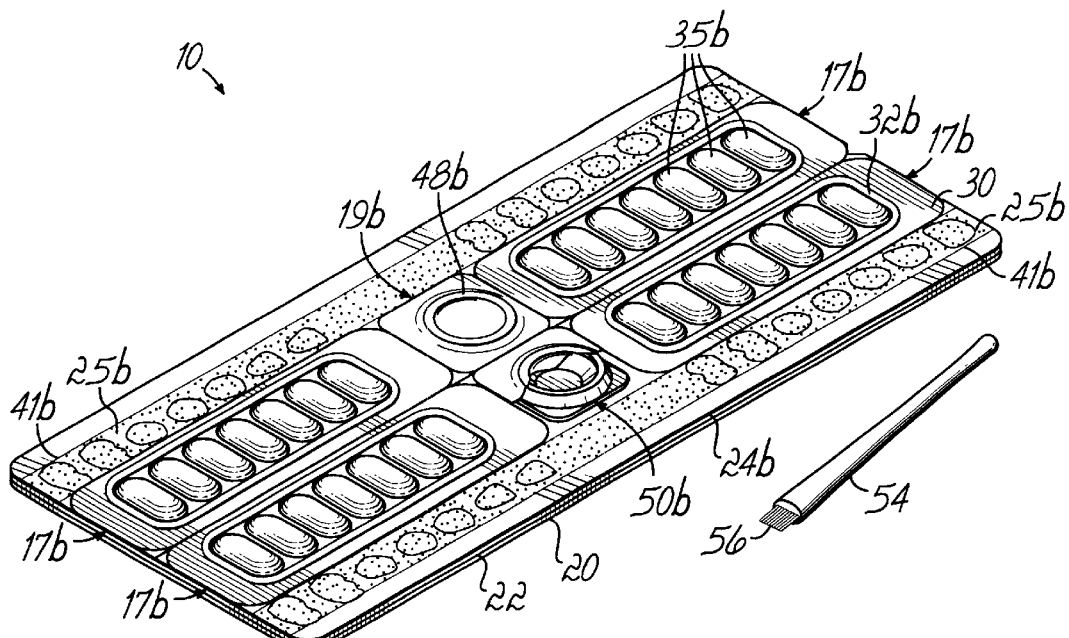
FIG. 2B is an assembled isometric view similar to FIGS. 2 and 2A of an orthodontic adhesive delivery system according the embodiment of FIG. 1B.
Figure 3B:
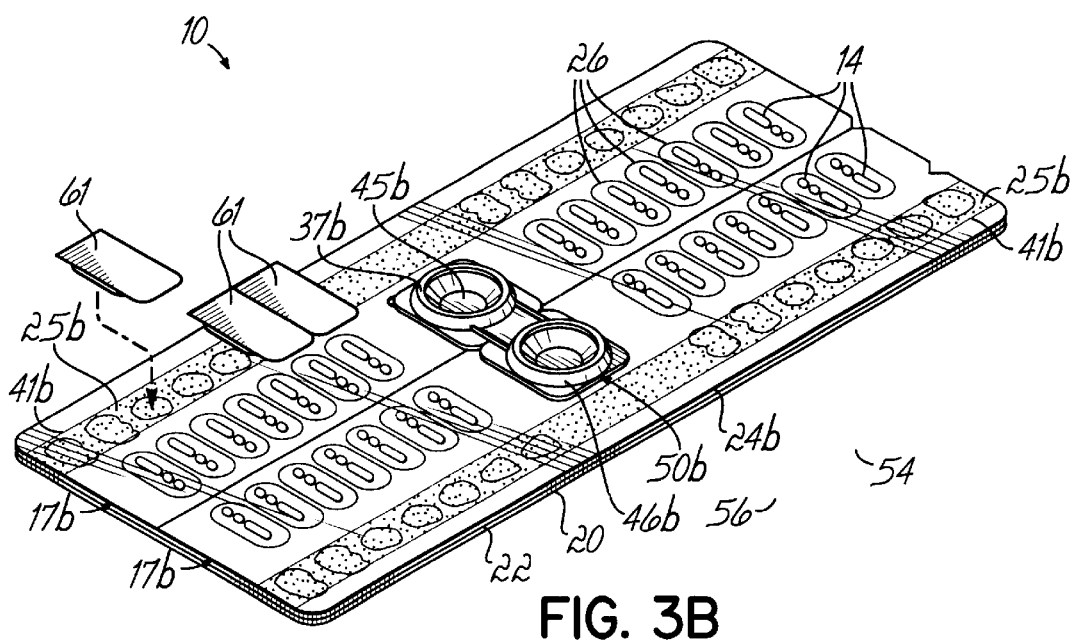
FIG. 3B is an isometric view, similar to FIGS. 3 and 3A, of an orthodontic adhesive delivery system of the embodiment of FIG. 1B prepared for use, and with individual prepackaged orthodontic appliances provided in association with the respective adhesive doses.

In the embodiment of FIG. 1B, there is provided a cup assembly 50b containing sealer-primer for the pre-coating of the teeth to which the adhesive doses 14 are to be applied for securing appliances to the teeth. The cup assembly 50b contains two hollow circular bowl shaped recesses 45b formed in an integral piece of molded plastic 46b. The cavities 45b may contain a one part sealer-primer or each of the parts of multiple part sealer-primer isolated from each other. The cup assembly 50b may be pre-filled by the supplier of the system 10b or may be provided empty to be filled by the orthodontist or orthodontic assistant. A cover for the cup assembly 50b may be formed by die cutting area 19b in the center of the foil and plastic cover 16b and bonded to the lip 37b of the rim of the cavities 45b along a circular area 48b of the cover 19b. The molded plastic piece 46b is mounted to the center of the surface layer 24b of the substrate 12b by inserting pegs 49 integrally molded on the bottom of the plastic piece 46b into holes 81 in the substrate 12b and flattening the tips of the pegs from the bottom of the substrate 12b with a heated platen. When so mounted, the bottom of the plastic piece 46b beneath the cavities 45b extends into holes 82 provided in the substrate 12b. A fully assembled and sealed system 10a is illustrated in FIG. 2B. The brush or applicator 54 may be provided to form a kit similar to the kit 55a illustrated in FIG. 4A. By dipping the tip 56 of the brush or applicator 55a into sealer-primer in the cavities 45b, sealer-primer can be transferred to the teeth.

Use of the system 10b can be carried out in the same manner as the use of the system 10a illustrated in FIGS. 4a and 5a and described above.

Figure 8:
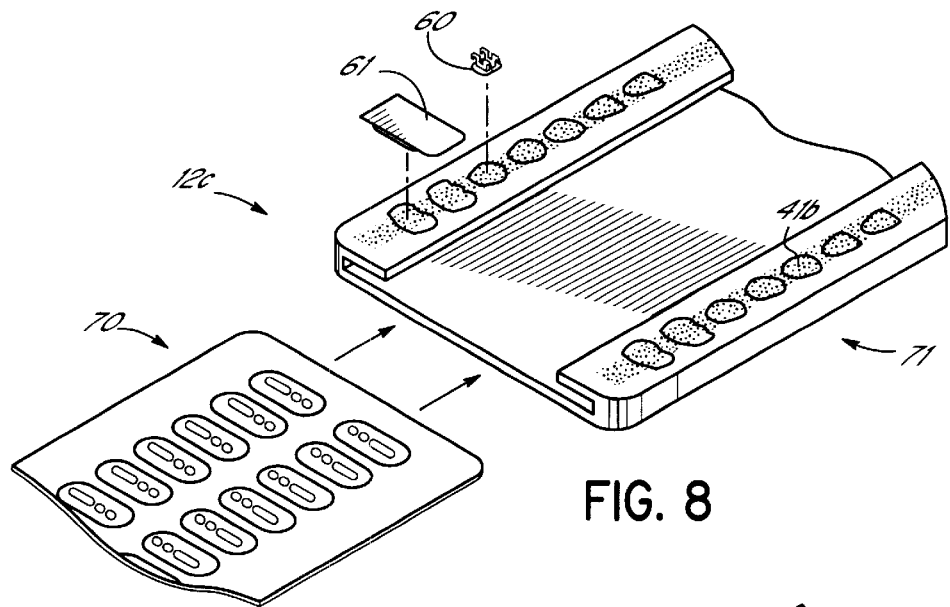
FIG. 8 is an isometric view of a substrate portion of the embodiments of the system of FIGS. 1 or 2 illustrating one manner in which the appliances and adhesive doses are associated, wherein orthodontic appliances mounted as a set, physically separate from but attachable to the adhesive bearing substrate.

While in the embodiments described above, pads 41 or mounting positions 41a are provided for supporting appliances next to associated adhesive doses, the substrates 12, 12a and 12b can alternatively be provided as two part cards 85, with a substrate card 70 carrying the adhesive doses 14 being supplied separate from an appliance mounting card 71 with appliances 60 or prepackaged appliances 61 mounted, and preferably premounted, thereon on mounting areas 41c, as illustrated in FIG. 8. In this way, mounted sets of appliances can be delivered by an appliance manufacturer to an orthodontist who can stock an assortment of these relatively long lived and relatively expensive appliance set assemblies, while the relatively shorter lived and relatively inexpensive adhesive-containing components stocked separately by the orthodontist and replaced if necessary to maintain a fresh supply of adhesive. When a case is ready for treatment, the adhesive carrying card 70 can be inserted into a slot in the appliance mounting card 71.

Figure 8A:
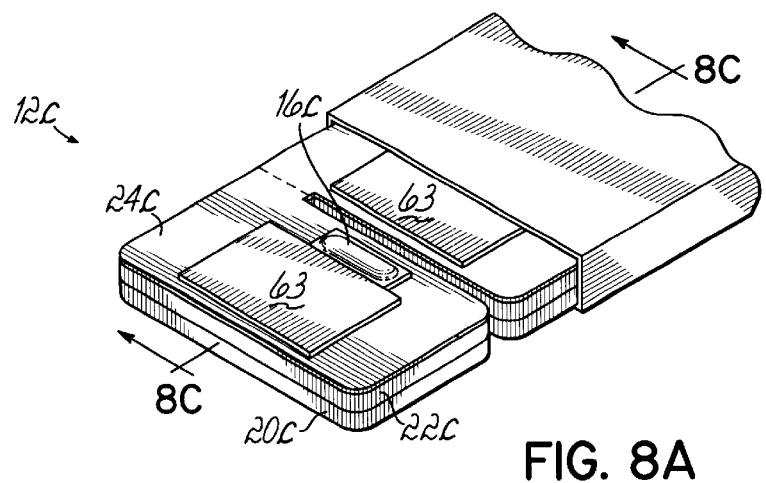
FIGS. 8A—8C are views illustrating another manner in which the orthodontic appliances and adhesive doses are associated, wherein individual orthodontic appliances are mounted individually to a single dose adhesive bearing substrate.
Figure 8B:
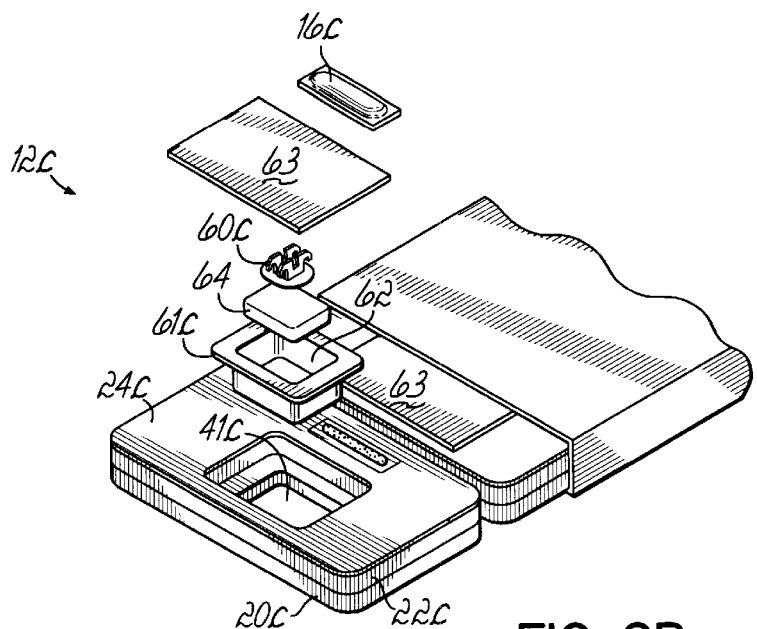
Figure 8C:
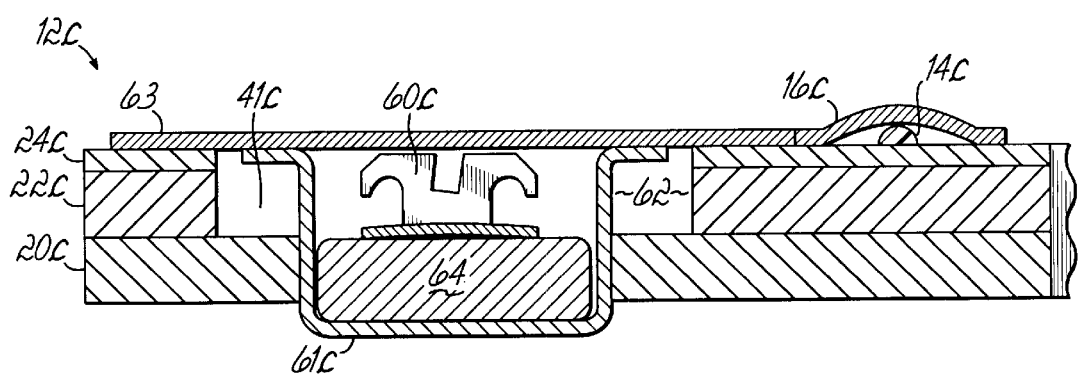

Certain features of the present invention can be utilized with individual orthodontic brackets, or in general with individual dental structures, by providing an adhesive delivery system 10c having a single dose card or substrate 12c, as illustrated in FIG. 8A. The single dose card 12c having bottom layer 20c, a core layer 22c and a top layer 24c having the properties of the layers 20, 22 and 24, described above, but differing in size. A rectangular opening 41c is provided in the substrate 12c to receive a single bracket package 61c that contains a single orthodontic bracket 60c, The package 61c may be configured to mount in the opening 41c in a "snap-in" manner as described in U.S. Pat. No. 5,354,199, or may be configured to otherwise attach. The bracket 60c is enclosed in a cavity 62 in the package 61c by a tape like lid 63 that is secured to the surface 24c of the card 12c by pressure sensitive adhesive (not shown) around the perimeter of the opening 41c. A foam cushion 64 may be provided to immobilize the bracket 60c when packaged in the cavity 62. The package 61c containing the bracket 60c can be attached to the card 12c either by a bracket manufacturer who supplies both the bracket and the adhesive delivery system 10c or by the orthodontist who procures the bracket and the adhesive separately.

A single adhesive transfer area 26c is provided on which is deposited a single dose quantity of orthodontic adhesive 14c. Covering the adhesive 14c is a cover assembly 16c, similar to those described above, that is secured to the surface 24c of the substrate 12c by pressure sensitive adhesive (not shown) around the perimeter of the area 26c so as to be separately removable to expose the adhesive 14c. When the covers 63 and 16c are removed at chairside by the orthodontist to expose the bracket 61c and the adhesive 14c, the bracket 61c can be removed by the orthodontist from the cavity 62 using tweezers, for example; and with the tweezers, the bracket 61c can be swiped along the surface 24c to scoop up the adhesive dose 14c and then to immediately place the bracket on a patient's tooth, as described above.

Those skilled in the art will appreciate that the application of the present invention herein is varied, that the invention is described in preferred embodiments, and that additions and modifications can be made without departing from the principles of the invention.

What is claimed is:

1. An orthodontic adhesive delivery system comprising:

a substrate having an adhesive supporting surface having at least one adhesive transfer area;

at least one single-appliance dose quantity of orthodontic dental adhesive on the at least one adhesive transfer area;

means for attaching an orthodontic appliance to the substrate and associating the appliance with the at least one single-appliance dose quantity of orthodontic dental adhesive; and a cover sealed to the substrate enclosing the at least one adhesive transfer area and maintaining the at least one single dose of adhesive separate from said appliance.

2. An orthodontic appliance system including the delivery system of claim 1 and further comprising:

an orthodontic appliance attachable to the substrate and maintained separate from the at least one single dose of adhesive.

3. The orthodontic appliance system of claim 2 further comprising:

a single appliance package having the appliance sealed therein and attached to the substrate.

4. The orthodontic adhesive delivery system of claim 1 wherein:

the at least one adhesive transfer area includes a plurality of separate adhesive transfer areas;

the at least one single-appliance dose quantity of orthodontic dental adhesive includes a plurality of single-appliance dose quantities of orthodontic dental adhesive, each supported on a separate one of the plurality of adhesive transfer areas on the adhesive supporting surface of the substrate.

5. The adhesive delivery system of claim 1 wherein:

the adhesive supporting surface of the substrate is conformable to a surface of an object contacting a transfer area so as to facilitate the clean transfer of adhesive to said object.

6. A dental adhesive delivery system comprising:

a substrate having an adhesive supporting surface having at least one adhesive transfer area;

at least one single-appliance dose quantity of dental adhesive on the at least one adhesive transfer area;

a cover sealed to the substrate so as to form at least one enclosure covering the at least one adhesive transfer area of the adhesive supporting surface of the substrate and containing the at least one single dose of adhesive; and a cup fixed to the substrate for holding a liquid primer.

7. The dental adhesive system of claim 6 further comprising:

the liquid primer contained in the cup and an openable cover sealing the liquid primer in the cup.

8. A dental adhesive delivery system comprising:

a substrate having an adhesive supporting surface having at least one adhesive transfer area;

at least one single dose quantity of dental adhesive on the at least one adhesive transfer area; and the single dose quantity of dental adhesive being dispensed onto the at least one adhesive transfer area in a pattern including a nominal dose quantity of adhesive and one or more separate supplemental fractional dose quantities spaced from the nominal dose.

9. A dental adhesive delivery system comprising:

a substrate having an adhesive supporting surface having at least one adhesive transfer area;

at least one quantity of dental adhesive on the at least one adhesive transfer area; and the quantity of dental adhesive being dispensed onto the transfer area in a configuration including at least a nominal minimum quantity sufficient to effectively bond an appliance to a tooth; and the quantity of dental adhesive being a multiple part chemically curable adhesive having the parts each dispensed in a physically distinct region in the configuration on the substrate.

10. An orthodontic adhesive delivery system comprising:

a substrate having an adhesive supporting surface having a plurality of adhesive transfer areas:

a quantity of orthodontic dental adhesive on each of the adhesive transfer areas: and a cover sealed to the substrate so as to form at least one enclosure covering at least one of the adhesive transfer areas of the adhesive supporting surface of the substrate and containing the quantity of adhesive;

the substrate having the transfer areas thereon and having thereon a plurality of attachment areas, each for attaching an orthodontic appliance thereto so as to constrain the appliance in a ready position relative a transfer area having a quantity of adhesive thereon.

11. A dental adhesive delivery system comprising:

a substrate having an adhesive supporting surface;

a quantity of dental adhesive on the adhesive supporting surface of the substrate; and a cover enclosing the adhesive;

the quantity of dental adhesive being chemically curable adhesive having multiple parts, each part being deposited in a different one of a plurality of physically distinct regions on the substrate.

12. A method of supplying an adhesive comprising:

providing a substrate having an adhesive supporting surface;

dispensing at least one quantity of dental adhesive onto an adhesive transfer area on the adhesive supporting surface of the substrate; and enclosing the quantity of the dental adhesive on the adhesive supporting surface with a cover by sealing the cover to the substrate and forming an enclosure covering the adhesive transfer area of the adhesive supporting surface and containing the adhesive so as to separate the adhesive from, and maintain the adhesive out of contact with, an appliance.

13. An orthodontic appliance delivery system comprising:
a substrate having an adhesive supporting surface;
a single dose quantity of dental adhesive on the adhesive supporting surface of the substrate;
an orthodontic appliance package having an orthodontic appliance therein;
means for attaching the package to the substrate;
a cover sealed to the substrate enclosing the adhesive separate from the appliance.

14. The system of claim 13 wherein:
the means for attaching include structure configured to snap fit the package into an opening on the substrate.

15. The system of claim 13 further comprising:
a plurality of single dose quantities on the adhesive each on a supporting surface of the substrate; and
a plurality of packages each having a orthodontic appliance therein.

16. A dental adhesive delivery system for presenting a plurality of quantities of adhesive for pickup and transfer to an orthodontic appliance, the system comprising:
a substrate having an adhesive supporting surface having a plurality of adhesive transfer areas thereon at which said surface is conformable to an edge of an object during transfer of adhesive from the substrate by the scooping of the adhesive from the surface with the object;
at least quantity of dental adhesive on each adhesive transfer area; and
a cover sealed to the substrate so as to form at least one enclosure covering at least one adhesive transfer area of the adhesive supporting surface of the substrate and containing a quality of adhesive.

* * * * *

UNITED STATES PATENT AND TRADEMARK OFFICE
CERTIFICATE OF CORRECTION

PATENT NO.    : 6,482,003 B2
DATED         : November 19, 2002
INVENTOR(S)   : Dixon et al.

It is certified that error appears in the above-identified patent and that said Letters Patent is hereby corrected as shown below:

Column 4,
Line 43, reads "narrower than the, width" and should read -- narrower than the width --.

Column 7,
Line 51, reads "0.56-0.08 mm" and should read -- 0.05-0.08 mm --.

Column 9,
Line 47, reads "cover 16 The" and should read -- cover 16. The --.

Column 10,
Line 28, reads "en-face" and should read -- enface --.
Line 67, reads "transferred to, the" and should read -- transferred to the --.

Column 11,
Line 54, reads "outlines profiles 43" and should read -- outlines or profiles 43 --.

Column 13,
Line 31, reads "strips 41 b", it has the wrong font and spacing and should read -- strips 41b --.

Column 16,
Lines 31 and 34, colons should be semicolons.

Signed and Sealed this

First Day of July, 2003

JAMES E. ROGAN
*Director of the United States Patent and Trademark Office*